(12) United States Patent
Heinz

(10) Patent No.: US 7,951,200 B2
(45) Date of Patent: May 31, 2011

(54) VERTEBRAL IMPLANT INCLUDING PREFORMED OSTEOCONDUCTIVE INSERT AND METHODS OF FORMING

(75) Inventor: Eric S Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1120 days.

(21) Appl. No.: 11/485,259

(22) Filed: Jul. 12, 2006

(65) Prior Publication Data

US 2008/0015692 A1    Jan. 17, 2008

(51) Int. Cl.
*A61F 2/44*     (2006.01)
(52) U.S. Cl. .................................. 623/17.11
(58) Field of Classification Search ............... 623/17.11, 623/17.15, 17.16
See application file for complete search history.

(56) References Cited

U.S. PATENT DOCUMENTS

| | | | |
|---|---|---|---|
| 4,911,718 A * | 3/1990 | Lee et al. | 623/17.15 |
| 5,171,281 A * | 12/1992 | Parsons et al. | 623/17.15 |
| 5,443,514 A | 8/1995 | Steffee | |
| 5,609,635 A | 3/1997 | Michelson | |
| 6,096,080 A | 8/2000 | Nicholson et al. | |
| 6,224,630 B1 | 5/2001 | Bao et al. | |
| 6,547,823 B2 | 4/2003 | Scarborough et al. | |
| 6,562,074 B2 | 5/2003 | Gerbec et al. | |
| 6,613,089 B1 | 9/2003 | Estes et al. | |
| 6,758,863 B2 | 7/2004 | Estes et al. | |
| 6,761,738 B1 | 7/2004 | Boyd | |
| 6,855,167 B2 | 2/2005 | Shimp et al. | |
| 7,066,960 B1 | 6/2006 | Dickman | |
| 2004/0138591 A1 | 7/2004 | Iseki et al. | |
| 2005/0136764 A1 * | 6/2005 | Sherman et al. | 442/103 |
| 2005/0228498 A1 | 10/2005 | Andres | |
| 2005/0256582 A1 | 11/2005 | Ferree | |
| 2006/0116774 A1 | 6/2006 | Jones et al. | |

* cited by examiner

Primary Examiner — Thomas C Barrett
Assistant Examiner — Nicholas Woodall

(57) ABSTRACT

A vertebral implant for insertion into a patient includes an insert formed from an osteoconductive material and further including a biocompatible polymer body that is formed into the insert. The insert may extend over part or substantially the entire bone contact surface of the implant. The insert includes a bone contact surface and a substrate interface. The implant may include fibers that extend across the substrate interface from the insert to the body. The insert may be thin relative to the overall thickness of the implant. The insert may be preformed. The insert may be formed using a molding process. The body may be molded onto the insert.

6 Claims, 7 Drawing Sheets

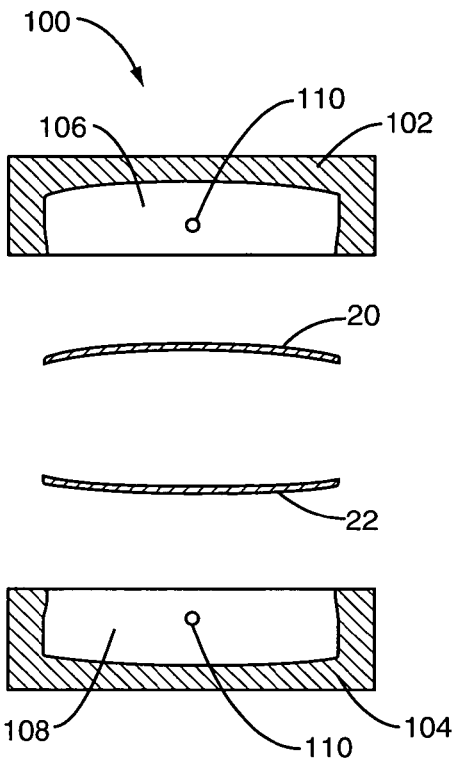
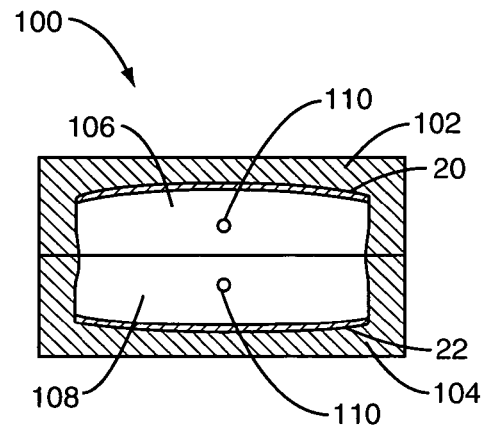
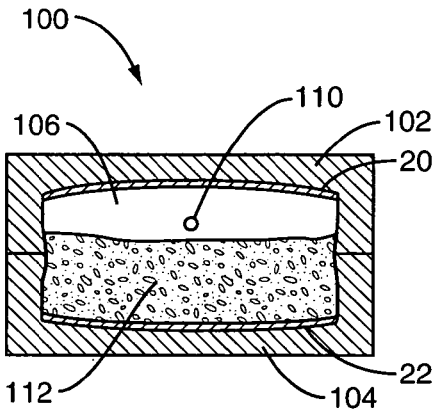
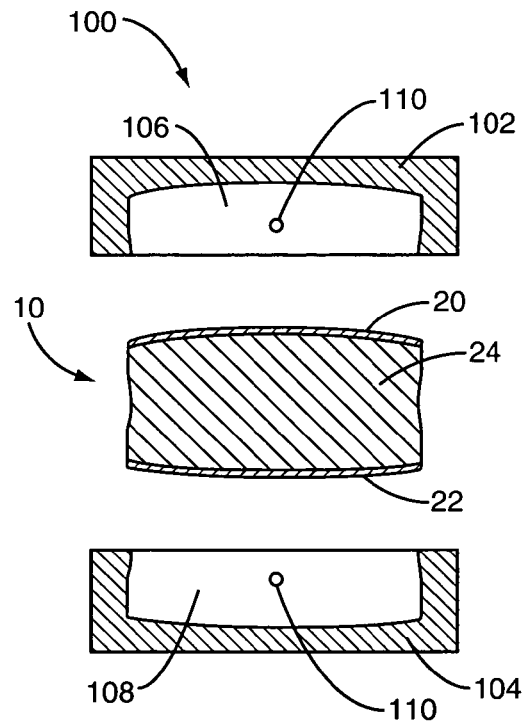
FIG. 5A  FIG. 5B  FIG. 5C  FIG. 5D

VERTEBRAL IMPLANT INCLUDING PREFORMED OSTEOCONDUCTIVE INSERT AND METHODS OF FORMING

BACKGROUND

Spinal implants are often used in the surgical treatment of spinal disorders such as degenerative disc disease, disc herniations, curvature abnormalities, and trauma. Many different types of treatments are used. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies.

Implants such as these may be positioned between vertebral bodies, with superior and inferior surfaces placed in contact with the vertebral bodies. Often, the bone-contact surfaces of these implants are configured with a surface texture, surface features, and natural or synthetic bone growth stimulators to promote osseointegration of the implant. Recent innovations in implant materials have produced a new generation of implants constructed from polymers such as UHMWPE or PEEK. These polymer materials may offer a variety of advantages, including improved strength, reduced weight, and desirable mechanical characteristics. Unfortunately, the polymers are not naturally osteoconductive. Thus, implant constructed from these polymers may not sufficiently fuse with the vertebral bodies. Ineffective fusion at the bone-contact surface may lead to subsidence of the vertebral implants over time, and often leads to spinal instability, angular deformities, and planar translations.

SUMMARY

Illustrative embodiments disclosed herein are directed to a vertebral implant for insertion into a patient includes an insert and a body. The insert may be formed from an osteoconductive material and the body may include a biocompatible polymer that is formed into the insert. The insert may extend over part or substantially the entire bone contact surface of the implant. Accordingly, the insert includes a first surface that is the bone contact surface and a second surface that is a substrate interface. The implant may include fibers that extend across the substrate interface from the insert to the body. The fibers may be disposed in a matrix. Some exemplary fibers include carbon fibers and metal filaments. The insert may be constructed from a braided or woven fabric of biocompatible material. The fibers may be oriented transverse to the substrate interface. The insert may be thin relative to the overall thickness of the implant. The insert may be preformed. For instance, the insert may be formed using a molding process, including but not limited to compression molding or injection molding. The body may be molded onto the insert. For instance, the insert may be positioned into a mold cavity and the biocompatible polymer forced into contact with to cure in secured attachment to the insert. Anchor features may be incorporated on the insert to further secure the adhesion between the insert and the body.

BRIEF DESCRIPTION OF THE DRAWINGS

FIGS. 5A-D illustrate exemplary process steps by which osteoconductive inserts may be formed onto an implant according to one embodiment;

DETAILED DESCRIPTION

Figure 1:
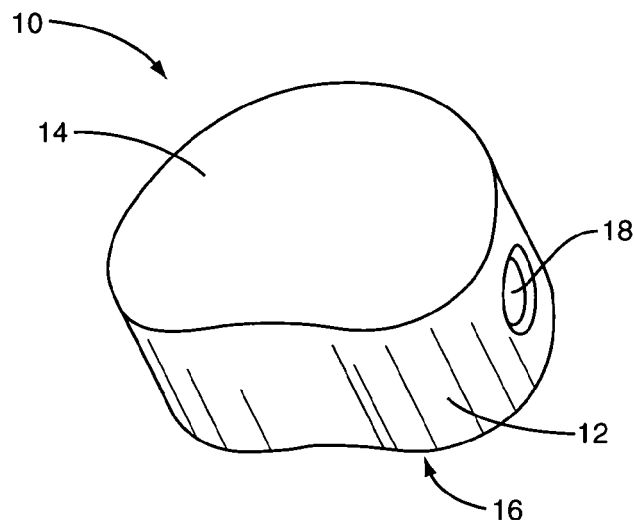
FIG. 1 is a perspective view of a vertebral implant according to one or more embodiments.

The various embodiments disclosed herein relate to a vertebral implant in which bone-contact surfaces are constructed with an osteoconductive insert. The number 10 in FIG. 1 generally identifies one example of an implant including an osteoconductive insert. The representative vertebral implant 10 is a disc replacement implant that is inserted between vertebral bodies of a patient as part of a disc replacement surgery. The vertebral implant 10 may be constructed, at least partially, from biocompatible polymers, such as polyethylene, UHMWPE, and implantable grade polyetheretherketone (PEEK) or other similar materials (e.g., PAEK, PEKK, PEK, PEEKK and PEKEKK). The exemplary vertebral implant 10 includes a perimeter wall 12 that extends between a superior surface 14 and an inferior surface 16. The superior surface 14 and inferior surface 16 are bone-contact surfaces in that they are positioned adjacent to and facing a vertebral endplate once the vertebral implant 10 is inserted into a patient.

The vertebral implant 10 shown in FIG. 1 includes a kidney shape, though other shapes may be used. In further embodiments, the vertebral implant 10 may take on other types of configurations, such as, for example, a circular shape, semi-oval shape, bean-shape, D-shape, elliptical-shape, egg-shape, or any other shape that would occur to one of skill in the art. The vertebral implant 10 may take on substantially solid configurations, such as, for example, block-like or plate-like configurations that do not define an open inner region. In other embodiments, the vertebral implant 10 could also be described as being annular, U-shaped, C-shaped, V-shaped, horseshoe-shaped, semi-circular shaped, semi-oval shaped, or other similar terms defining an implant including at least a partially open or hollow construction.

The exemplary vertebral implant 10 includes one or more apertures 18 disposed about the perimeter wall 12 that provide a location at which to grasp the vertebral implant 10 during surgical installation. In some instances, the vertebral implant 10 is constructed of a material that is solid, but somewhat flexible or compressible. Thus, the apertures 18 may contribute to the overall flexibility and/or compressibility of the vertebral implant 10.

Figure 2:
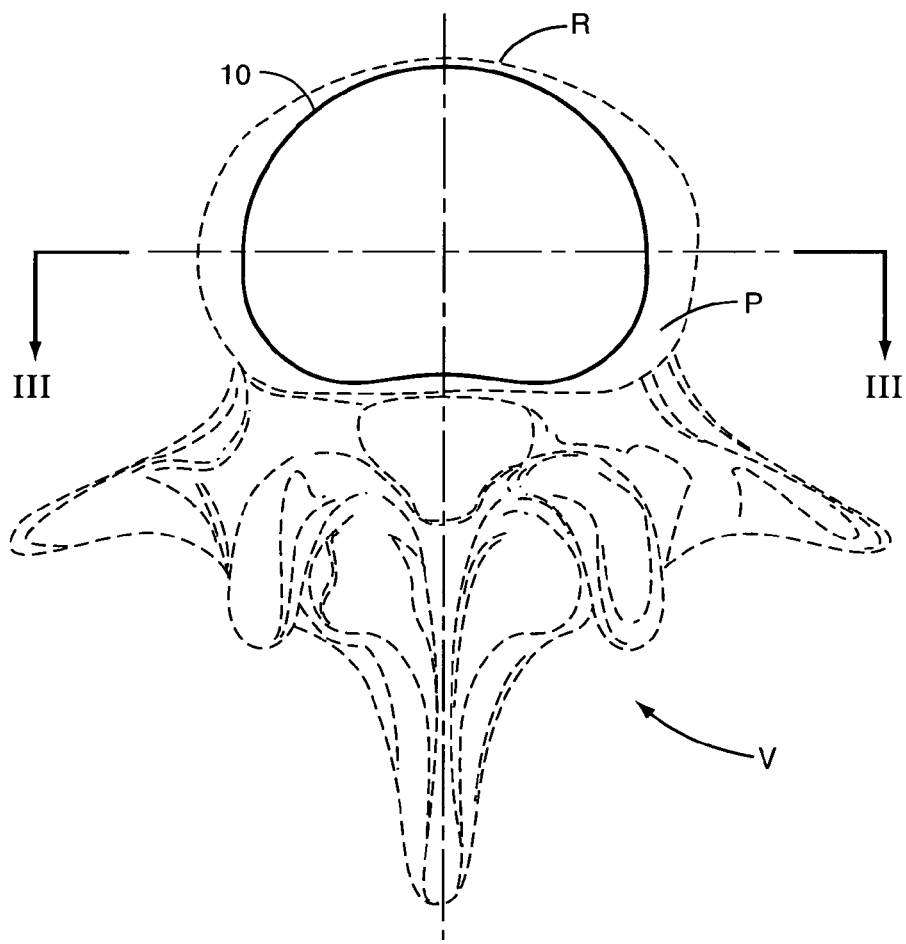
FIG. 2 is a top view of a vertebral implant according to one or more embodiments shown relative to a vertebral body.
Figure 3:
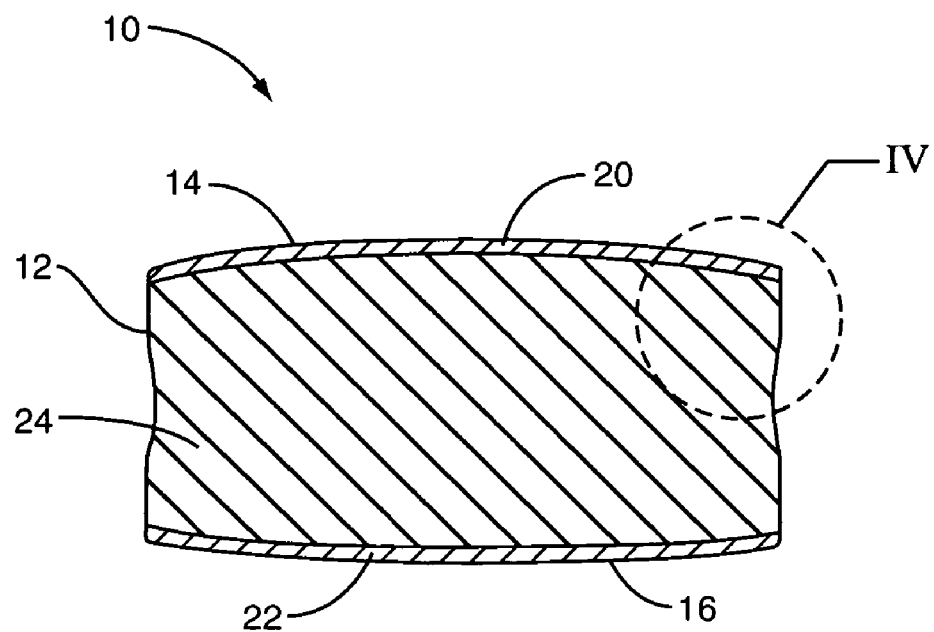
FIG. 3 is a section view of a vertebral implant according to one or more embodiments.

FIG. 2 depicts a top view of the exemplary vertebral implant 10 oriented relative to a vertebral body V, which is depicted in dashed lines. The vertebral implant 10 is positioned substantially within the cortical rim R of the vertebral body V. Further, the vertebral implant 10 is positioned in contact with one of the end plates P of the vertebral body V. Accordingly, the vertebral implant 10 includes a superior surface 14 and an inferior surface 16 that contact the bony end plates P of vertebral bodies V. Improved results may be obtained if the superior surface 14 and inferior surface 16 of the implant 10 fuse with the end plates P.

Where the implant 10 is constructed of a generally non-osteoconductive material, an osteoconductive insert may be formed into the implant to promote bone growth at the superior 14 and inferior 16 surfaces of the implant 10. To that end, FIG. 3 shows a section view of the vertebral implant 10 taken from the direction indicated by the section lines in FIG. 2. The section view in FIG. 3 shows that the implant 10 is constructed of an intermediate portion 24 and two inserts 20, 22. Generally, the intermediate portion 24 may be constructed of a non-osteoconductive polymer while inserts are constructed from osteoconductive materials. In one embodiment, the inserts 20, 22 are formed from a material or with a construction that provides a greater degree of osteoconduction than the intermediate portion 24. The inserts 20, 22 are disposed at the superior 14 and inferior 16 surfaces of the implant 10 and provide an interface surface into which bone growth is permissible.

The inserts 20, 22 may be constructed from an osteoconductive or osteoinductive matrix that includes materials such as collagen, carbon fibers, including continuous or chopped carbon fibers. The inserts may include carbon nano-fibers, or metallic filaments including titanium, tantalum, or stainless steel. The inserts 20, 22 may be constructed from a composite matrix of non-osteoconductive polymers filled with osteoconductive materials. The inserts 20, 22 may be constructed from a braided or woven fabric of biocompatible material. In general, the inserts 20, 22 may be thin relative to the overall height of the implant 10. For example, the inserts 20, 22 may have a thickness between about 1 and 10 mm. In one embodiment, the inserts 20, 22 have a thickness between about 3 mm and about 5 mm. The relatively thin nature of the inserts advantageously permits osseointegration while preserving the overall structural characteristics of the implant 10.

As indicated, the inserts 20, 22 may include osteoconductive fibers. These fibers 26 are depicted graphically in FIG. 4, which shows a detailed portion of the section view provided in FIG. 3. In one embodiment, the fibers 26 are oriented randomly. In one embodiment, the fibers 26 are oriented at least partially transverse to an interface surface 28 between the insert 20 (or 22) and the intermediate portion 24. In one embodiment, the fibers 26 extend through the interface surface 28 so that they are anchored in each of the insert 20 and the intermediate portion 24. The fibers 26 may include carbon fibers, metal filaments, or fibers from a woven or braided biocompatible material.

For the various embodiments disclosed herein, FIGS. 5A-5D depict exemplary process steps that may be performed to join the osteoconductive inserts 20, 22 to the intermediate portion. The process steps generally illustrate a molding process whereby the intermediate portion 24 is molded onto pre-formed inserts 20, 22. The inserts 20, 22 may be formed through a separate molding process, including compression molding, injection molding, or a machining operation where the inserts are cut from stock material.

The exemplary process contemplates a mold 100 that is used to injection mold the intermediate portion 24 onto the inserts 20, 22. Other techniques may be used and the present illustration is provided merely as one possible approach. In a first step shown in FIGS. 5A and 5B, the preformed inserts 20, 22 are positioned within a mold cavity 106, 108 of respective mold halves 102, 104. Once the inserts 20, 22 are positioned as desired, the mold is closed as illustrated in FIG. 5B. In the embodiment depicted, the mold halves 102, 104 are substantially equilateral. That is, the mold halves 102, 104 form a parting line near the midline of the implant 10. Those skilled in the art will recognize that more complex mold configurations including multiple components may be required depending on implant complexity and geometry. The illustrated mold halves 102, 104 include injection ports 110 through which resin material is forced to fill the mold 100.

Once the mold 100 is closed, resin material 112 from which the intermediate portion is formed is injected through the injection ports 110 and into the mold cavities 106, 108. FIG. 5C illustrates the resin material 112 in fluid form partially filling the mold cavities 106, 108. After a sufficient amount of additional resin material 112 is added to completely fill the mold cavities 106, 108, the resin material 112 is allowed to set and harden. Once the resin material 112 has cured, the mold 100 is separated and the implant 10 may be removed as shown in FIG. 5D.

Figure 4:
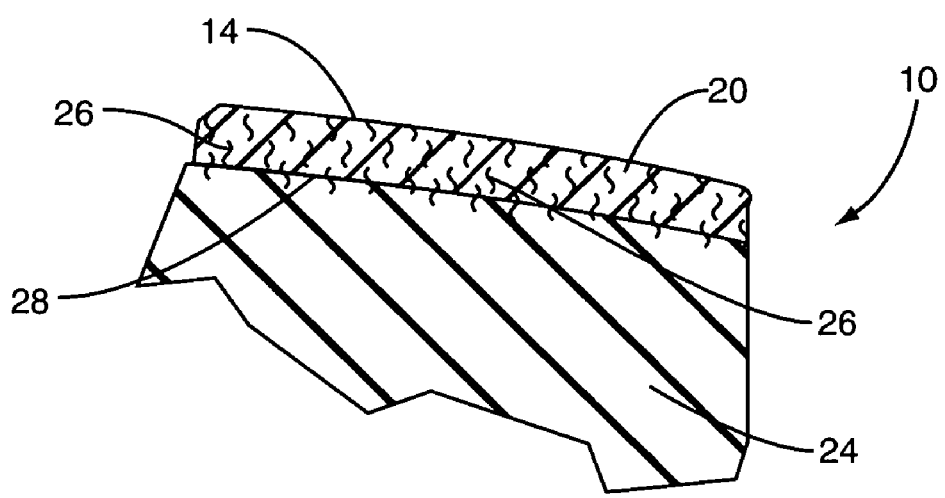
FIG. 4 is a detail view of the vertebral implant of FIG. 3.

In the embodiment illustrated in FIGS. 3-5, the inserts 20, 22 abut the intermediate portion 24. Adhesion between the components 20, 22, 24 may be improved via fiber orientation as shown above. Adhesion may be improved where the inserts 20, 22 are at least partially porous so that resin material may expand into the inserts 20, 22 during the process of forming the intermediate portion 24 onto the inserts 20, 22. Alternately, the inserts 20, 22, may include anchor features as depicted in the embodiments shown in FIGS. 6 and 7.

Figure 6:
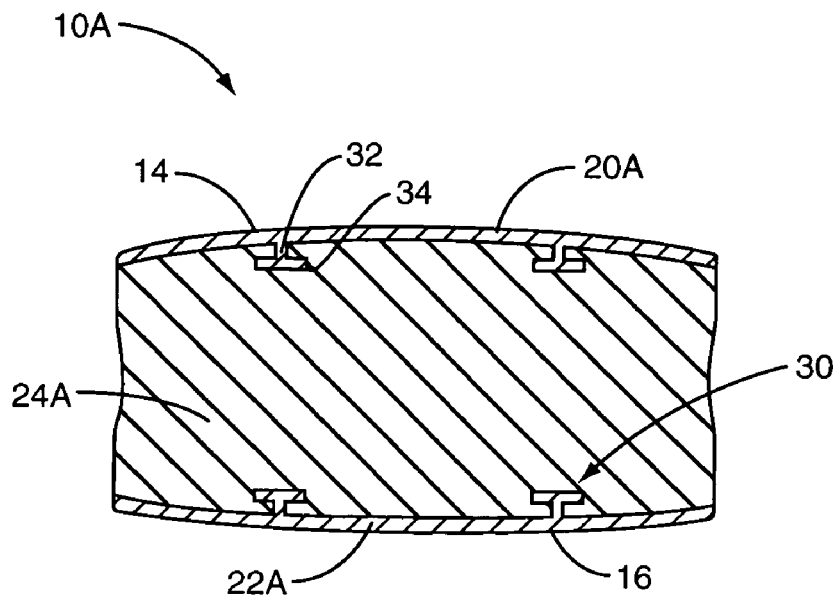
FIG. 6 is a section view of a vertebral implant according to one or more embodiments.

FIG. 6 shows an implant 10A including inserts 20A, 22A, and an intermediate portion 24A. In the illustrated embodiment, the inserts 20A, 22A include a plurality of anchors 30 comprising a stem portion 32 and an enlarged head portion 34. In embodiments where the injectable resin 112 comprises a curable liquid that forms the intermediate portion 24A, the cured material may harden in the undercuts adjacent the stem portion 32, between the head portion 34 and the inserts 20A, 22A. The anchors 30 may provide a more secure bond between the intermediate portion 24A and the inserts 20A, 22A.

Figure 7:
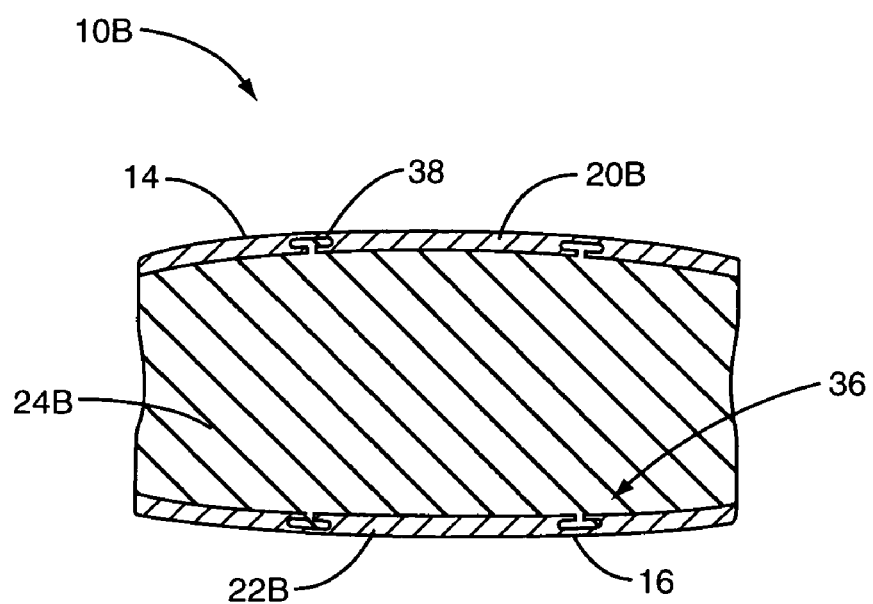
FIG. 7 is a section view of a vertebral implant according to one or more embodiments.

Similarly FIG. 7 shows an implant 10B including inserts 20B, 22B, and an intermediate portion 24B. In the illustrated embodiment, the inserts 20B, 22B include a plurality of anchors 36 comprising a recess 38. As above, the injectable resin 112 may harden in the recesses 38. The anchors 36 may provide a more secure bond between the intermediate portion 24B and the inserts 20B, 22B.

Figure 8:
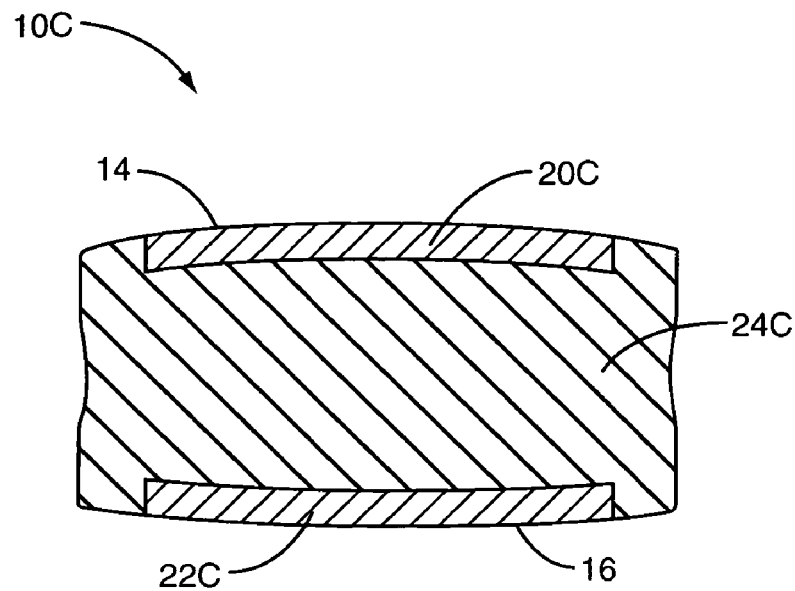
FIG. 8 is a section view of a vertebral implant according to one or more embodiments.

In embodiments described above, the inserts 20, 22 have formed substantially the entire superior 14 and inferior surfaces 16 of the implant 10. However, this is not expressly required. The inserts 20, 22 may extend over some area that is less than the entire bone-contact surface. For instance, FIG. 8 shows an embodiment of an implant 10C in which the osteoconductive inserts 20C, 22C are disposed at the superior 14 and inferior 16 surfaces of the implant 10C. However, the inserts 20C, 22C form less than the entire superior 14 and inferior 16 surfaces, respectively. The intermediate portion 24C forms the remaining portion of the superior 14 and inferior 16 surfaces.

Figure 9:
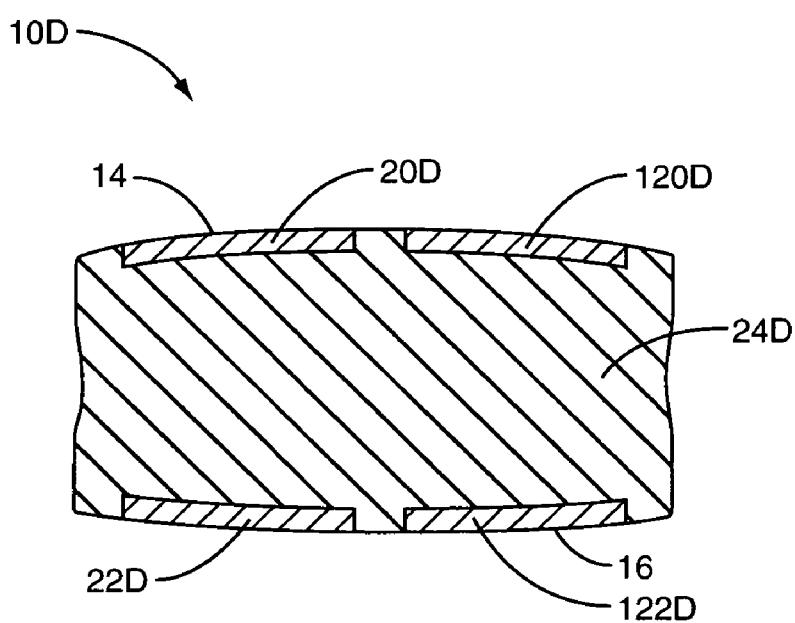
FIG. 9 is a section view of a vertebral implant according to one or more embodiments.

In addition, there is no express limitation on the number of inserts 20, 22 that are included at the bone contact surfaces of the implant 10. Thus, for example, FIG. 9 shows an implant 10D in which the superior surface 14 includes a plurality of osteoconductive inserts 20D, 120D. In the present embodiment, two inserts 20D, 120D are provided at the superior surface 14, though a larger number of inserts 20D, 120D may be provided. Likewise, the inferior surface 16 includes two osteoconductive inserts 22D, 122D, though a larger number may be included in the implant 10D.

Figure 10:
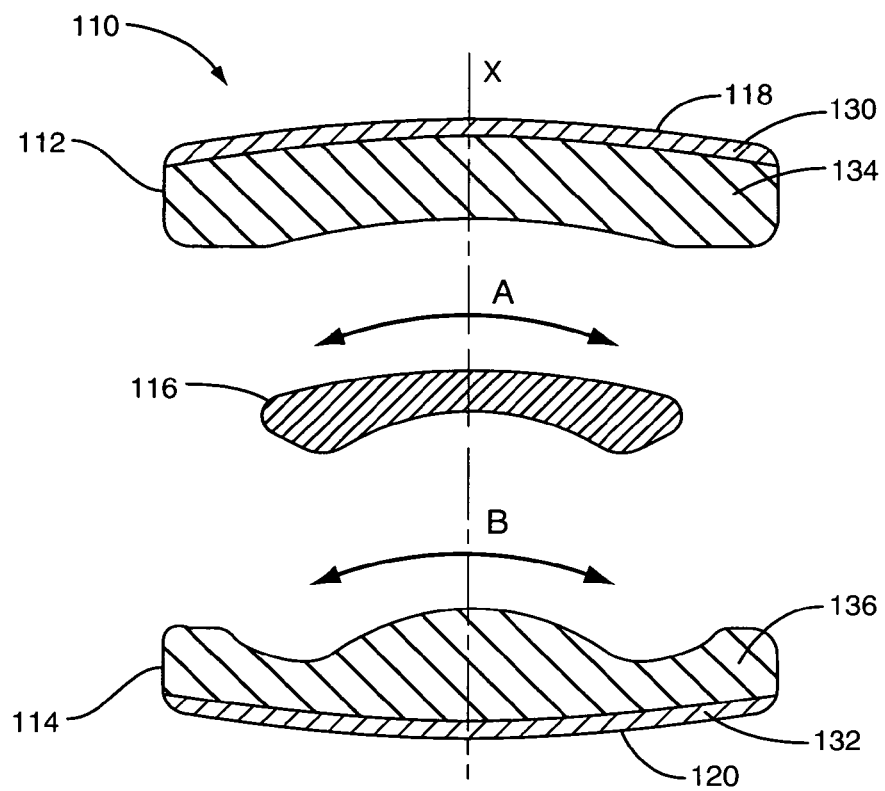
FIG. 10 is a section view of a vertebral arthroplasty implant according to one or more embodiments.

Embodiments described above have pertained to vertebral implants 10 in which superior and inferior bone contact surfaces are located on the same body. However, this is not expressly required. The curvature of the respective bone contact surfaces may be disposed in separate implants or separate implant members such as the vertebral implant 110 shown in FIG. 10. The vertebral implant 110 represents a spinal arthroplasty device and comprises three main components: a first end plate 112, a second end plate 114, and a nucleus 116. In the orientation shown, the first end plate 112 is a superior end plate while the second end plate 114 is an inferior end plate. Each end plate 112, 114 may include a respective bone interface surface 118, 120 that is placed in contact with a corresponding a vertebral member (not shown). The nucleus 116 is positioned between the end plates 112, 114. The interface between the nucleus 116 and each end plate 112, 114 is a sliding interface that allows for sliding motion of the nucleus 116 relative to the end plates 112, 114. The arrows labeled A and B in FIG. 10 illustrates this sliding motion. In the illustrated embodiment, each end plate 112, 114 is constructed with an osteoconductive insert 130, 132 that is formed onto a resin substrate 134, 136, respectively.

Figure 11:
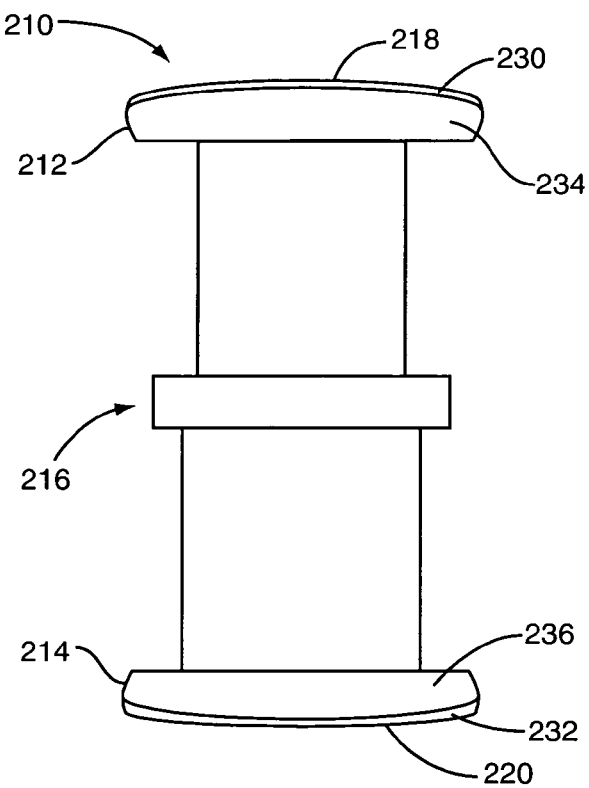
FIG. 11 is a side view of a corpectomy implant according to one or more embodiments.

The vertebral implant 110 shown in FIG. 10 is configured to restore motion between vertebral bodies. In other procedures, such as vertebrectomies or corpectomies, one or more vertebral bodies are removed and an implant is inserted in the space left by the removed vertebrae. These types of devices include multiple components similar to the implant 110. For example, FIG. 11 illustrates an exemplary corpectomy device 210 in which an expandable cage 216 is disposed between end plates 212, 214. Other types of devices may include spacers, rods, or other fixed or expandable members spanning a distance between first and second end plates 212, 214. As illustrated, osteoconductive inserts 230, 232 may be incorporated onto a non-osteoconductive resin substrate 234, 236 to promote bone growth at respective bone-contact surfaces.

An exemplary process for making the vertebral implants may include steps of providing an osteoconductive insert comprising a bone contact surface and a substrate interface, orienting a matrix of fibers to extend outward from the interface surface, and forming a body constructed at least partially from a biocompatible polymer into the substrate interface and around the matrix of fibers. Forming the body in this manner may include extending the matrix of fibers into the body between about one and two millimeters. Furthermore, it may be appropriate to orienting the matrix of fibers substantially transverse to the substrate interface. The osteoconductive insert may be positioned to cover substantially the entire bone contact surface of the vertebral implant. The matrix of fibers may comprise carbon fibers or metal fibers.

Another exemplary process for making the vertebral implants may include steps of preforming an osteoconductive insert, inserting the osteoconductive insert into a mold, introducing a biocompatible polymer into the mold and forcing the biocompatible polymer into contact with the insert, and causing the polymer to cure within the insert so that the insert forms a bone contact surface of the vertebral implant. These process steps may further include positioning the osteoconductive insert to form substantially all of the bone contact surface of the vertebral implant. The preforming process may include exemplary processes such as molding osteoconductive material to form the osteoconductive insert and forming a porous matrix of fibers into the osteoconductive insert. Furthermore, the step of forcing the polymer into contact with the insert further may cause the polymer to cure around a matrix of fibers that extend outward from an outer surface of the osteoconductive insert.

Figure 12:
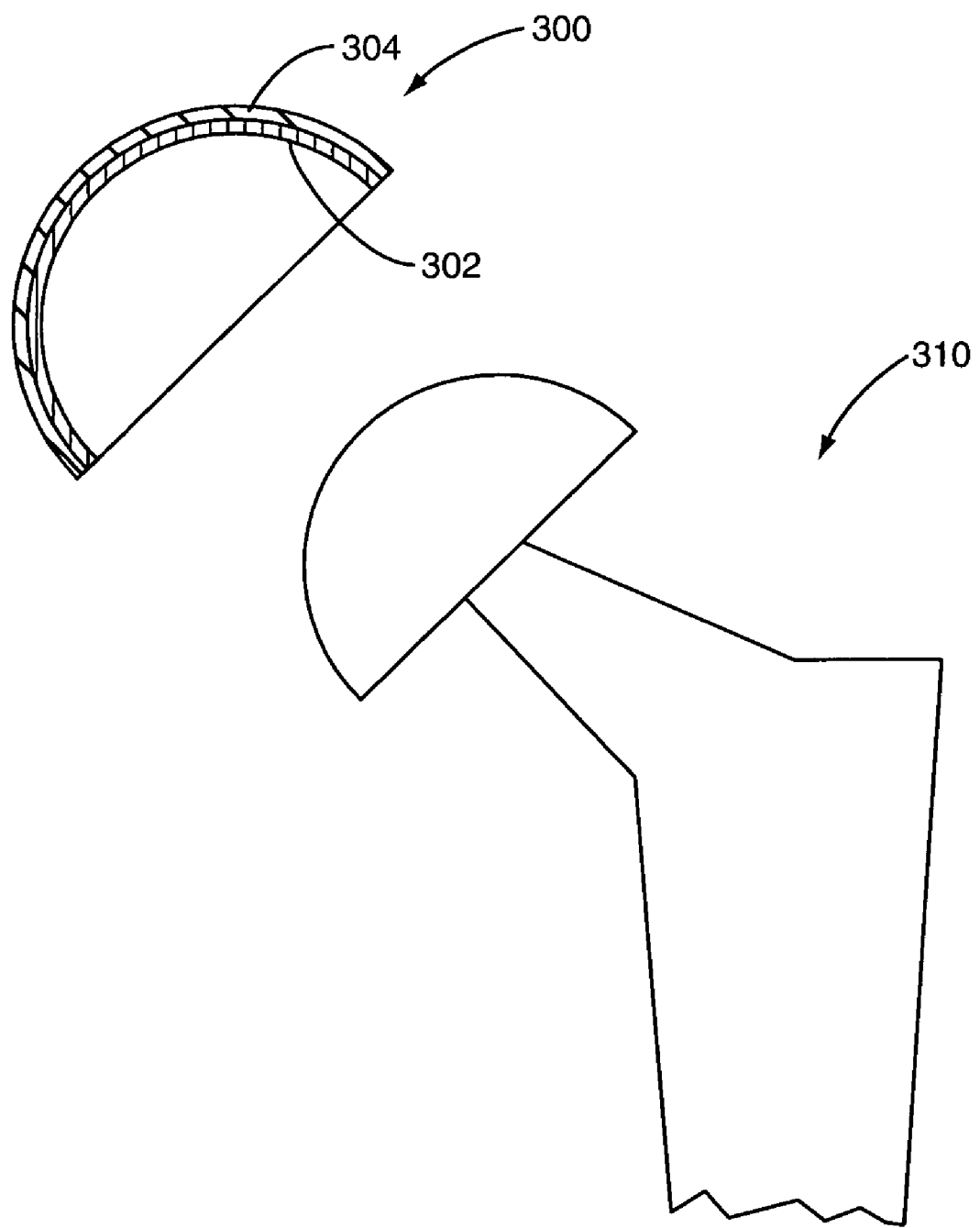
FIG. 12 is a side section view of an acetabular implant according to one or more embodiments.

The osteoconductive inserts are not limited to vertebral implants. For example, osteoconductive inserts may be incorporated into other orthopedic implants formed from a non-osteoconductive resin such as tibial and femoral knee components, hip stems, and acetabular cups 300 such as that shown in FIG. 12. The illustrated cup 300 includes a substrate portion 302 that is sized and shaped to accept a femoral stem 310. An osteoconductive insert 304 is formed onto the substrate 302. The acetabular cup 300 may be molded using the process steps similar to that depicted in FIGS. 5A-5D.

Furthermore, embodiments disclosed above have not included any particular surface geometry, coating, or porosity as are found in conventionally known vertebral implants. Surface features such as these are used to promote bone growth and adhesion at the interface between an implant and a vertebral end plate. Examples of features used for this purpose include, for example, teeth, scales, keels, knurls, and roughened surfaces. Some of these features may be applied through post-processing techniques such as blasting, chemical etching, and coating, such as with hydroxyapatite. The bone interface surfaces, including the osteoconductive inserts, may also include growth-promoting additives such as bone morphogenetic proteins. Alternatively, pores, cavities, or other recesses into which bone may grow may be incorporated via a molding process. Other types of coatings or surface preparation may be used to improve bone growth into or through the bone-contact surfaces. However, the inserts that include these types of features may still be formed and characterized by the aspects disclosed herein.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the implant 10 depicted in FIGS. 2-9 may be described as an ALIF device, implantable from an anterior approach. However, the osteoconductive inserts may be incorporated in other types of vertebral implants, including but not limited to TLIF or PLIF devices. The present embodiments are, therefore, to be considered in all respects as illustrative and not restrictive, and all changes coming within the meaning and equivalency range of the appended claims are intended to be embraced therein.

What is claimed is:

1. A vertebral implant device for insertion between vertebral bodies in a patient, the implant comprising:
   a preformed osteoconductive insert comprising a bone contact surface and a substrate interface; the preformed insert further comprising a matrix of fibers anchored therein and extending outward therefrom at the substrate interface approximately perpendicular to the substrate interface;

a body constructed at least partially from a biocompatible polymer; the body formed into the substrate interface;

wherein the matrix of fibers extends outward from the insert and through the interface substrate between the insert and the body and into the body; wherein said fibers are configured to improve adhesion between the insert and the body.

2. The vertebral implant device of claim 1 wherein the matrix of fibers comprises carbon fibers.

3. The vertebral implant device of claim 1 wherein the matrix of fibers comprises metal fibers.

4. A vertebral implant device for insertion between vertebral bodies in a patient, the implant comprising:

a preformed osteoconductive insert comprising a bone contact surface and a substrate interface; the insert having a thickness between the bone contact surface and the substrate surface of between about 1 and about 10 millimeters; and the insert including a plurality of fibers extending outwardly generally perpendicularly from the substrate interface;

a body constructed at least partially from a biocompatible polymer; the body formed into the substrate interface such that the body adheres to the fibers extending from the substrate interface of the insert.

5. The vertebral implant device of claim 4 wherein the insert forms substantially the entire bone contact surface for the vertebral implant.

6. The vertebral implant device of claim 4 wherein the insert forms less than substantially the entire bone contact surface for the vertebral implant.

* * * * *